(12) United States Patent
Hannappel

(10) Patent No.: US 10,011,828 B2
(45) Date of Patent: Jul. 3, 2018

(54) NON-DISRUPTIVE DNA ISOLATION FROM CORN SEEDS

(71) Applicant: Syngenta Participations AG, Basel (CH)

(72) Inventor: Ulrich Stephan Hannappel, Slater, IA (US)

(73) Assignee: Syngenta Participations AG, Basel (CH)

( * ) Notice: Subject to any disclaimer, the term of this patent is extended or adjusted under 35 U.S.C. 154(b) by 127 days.

(21) Appl. No.: 14/890,955

(22) PCT Filed: May 28, 2014

(86) PCT No.: PCT/EP2014/061036
§ 371 (c)(1),
(2) Date: Nov. 13, 2015

(87) PCT Pub. No.: WO2014/195199
PCT Pub. Date: Dec. 11, 2014

(65) Prior Publication Data
US 2016/0115472 A1  Apr. 28, 2016

Related U.S. Application Data

(60) Provisional application No. 61/830,242, filed on Jun. 3, 2013.

(51) Int. Cl.
| | | |
|---|---|---|
| C12N 15/10 | (2006.01) | |
| C12Q 1/68 | (2018.01) | |
| A01H 1/04 | (2006.01) | |
| C12Q 1/6895 | (2018.01) | |

(52) U.S. Cl.
CPC ........... *C12N 15/1003* (2013.01); *A01H 1/04* (2013.01); *C12Q 1/6895* (2013.01); *C12Q 2600/13* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS 7,832,143 B2    11/2010  Deppermann et al.
2006/0035227 A1*  2/2006  Minobe ............... C12Q 1/6895
                                                    435/6.11

FOREIGN PATENT DOCUMENTS

WO    2007103786 A2    9/2007
WO    2011119763 A1    9/2011

OTHER PUBLICATIONS

Junior et al Chapter 18 "DNA Extraction from Seeds". in Evolutionary Genetics and Molecular Biology. 2016. ( M. Micic (ed.) (Springer Science + Business Media, New York, USA), p. 265-276.*
Von Post et al. Euphytica. 2003. 130: 255-260.*
International Search Report for International Patent Application No. PCT/EP2014/061036 dated Aug. 11, 2014.
Wu et al., "Rapid and Reliable Purity Idnetification of F1 Hybrids of Maize (*Zea may* L.) Using SSR Marker," Maize and Genomics and Genetics, 2010, vol. 1, pp. 1-4.

* cited by examiner

*Primary Examiner* — Carla J Myers
(74) *Attorney, Agent, or Firm* — Christopher Leming

(57) ABSTRACT

This invention relates to systems and process for isolating DNA from biological materials such as seeds while retaining a viable seed for further use. The seed from which the DNA is isolated remains viable and is used or discarded based on the DNA analysis of the seed soak solution. The seed soak solution can have substantially all of the confounding maternal DNA from the seed eliminated from the seed soak solutions by employing intact seed pretreatments. This method is particularly useful for maize seed.

6 Claims, 16 Drawing Sheets
(16 of 16 Drawing Sheet(s) Filed in Color)

NON-DISRUPTIVE DNA ISOLATION FROM CORN SEEDS

RELATED APPLICATION INFORMATION

This application is a 371 of International Application No. PCT/EP2014/061036, filed 28 May 2014, which claims the benefit of U.S. Provisional Patent Application No. 61/830,242, filed 3 Jun. 2013, the contents of which are incorporated by reference herein.

FIELD OF THE INVENTION

This invention relates to systems and process for isolating DNA from biological materials such as seeds while retaining a viable seed for further use. The seed from which the DNA is isolated remains viable and is used or discarded based on the DNA analysis of the seed soak solution. The seed soak solution can have substantially all of the confounding maternal DNA from the seed eliminated from the seed soak solutions by employing intact seed pretreatments. This method is particularly useful for maize seed.

BACKGROUND OF THE INVENTION

Commercial seed industry research on plants results in genetic improvements in seed. A number of different processes can result in improved seeds, haploid/double haploid systems, traditional or genotype assisted breeding, mutation, transformation, etc. The improved seed when genetically stable is increased so that there is a large quantity of the improved seed for sale to growers. In the process of increasing lines or finding and developing stable lines the seed is planted and harvested and seed is selected over several seasons. Until the plant has a fixed and stable inheritable desired improvement, not all seeds express the improvement. In the breeding process seeds without the improvement from the population are removed prior to planting the next generation of seed. A statistical samplings which are tested for determining if the improvement is in the seed is used when bulking the seed population. The results of the test determine if there is seed that should be removed because they lack the improvement. This process lacks efficiency because it often results in loss of some desired seed and some maintenance of some undesired seed.

To overcome the deficiencies of statistical sampling, the seed industry has developed systems and methods of non-destructively sampling material from seeds for testing. Principally, the goal of these methods is to remove a portion of a seed, the 'seed chip' which is used for testing. The 'seed chip' or seed sample, often has extracted DNA analyzed for the desired seed characteristics. Depending on the seed sample test results, the correlated viable seed is used for planting or discarded.

Efficiencies in producing the seed chips and viable chipped seeds have been the focus of the development of mechanical devices for automating the process. Two types of automated seed "chipping" devices have been developed. Each have a device for removing material from a seed, one uses a brocade and the other uses a laser. These devices have a seed conveyer for conveying the seed to a compartment in a seed tray; and a sample conveyor for conveying the material removed from the seed to a corresponding compartment in a sample tray. The sample seed is used for DNA extraction which is tested. The viable seed is stored. And each process correlates the seed chips with the viable seed from which it was chipped. The chip is used for testing and the seed is discarded, stored or used for planting.

In operation these sample tray and seed tray locations have to be associated so that when the seed samples are tested, the test results can be employed to select or sort the seeds. These devices are set up to test large quantities of seed which results in two sets of tray storage, two sets of tray documentation, and two sets of locations that must be coordinated so that the association between the two sets sample seed and viable untested seed is maintained.

The prior art methods and devices for the automated system require two essential seed parts, the viable seed for planting and the seed sample, in other words, the chip for testing. The chip provided the seed DNA for testing. Although these different automated systems have different means for positioning seeds for cutting, for cutting the seed chip from the seed, for transporting seed and chip, etc., both of these systems are burdensome and complex. These seed chipping systems require a constant correlation to be kept between the two essential seed parts. The existing automated systems require a tray of seed material and a tray of the seed chips.

These systems require the use of two seed parts, each which are stored and handled separately but with a known association. This process requires that the corresponding chip and seed are correctly matched so that the test results for the chip will result in the removal of the correct undesired seed material. The present invention addresses the complexity of needing two essential seed parts and the need to track both the seed tray and the chip tray which cause a number of the existing complexities of the prior inventions.

SUMMARY OF THE INVENTION

The present invention does not require two essential seed parts to be tracked. In one embodiment the method of the present invention is developed for analyzing a population of seeds. In one embodiment, the seeds are corn seeds. The method has steps of exposing the seed endosperm, from individual seeds in a population of seeds while preserving germination viability of the seeds, and soaking the viable exposed seed in a non-disruptive DNA releasing or isolating solution thereby forming a seed solution from each of the individual seeds in the population and analyzing the seed solution for the presence or absence of one or more traits of interest. In one embodiment of the invention, the non-disruptive DNA releasing or isolating solution is an alkali solution. The alkali solution in some instances is sodium hydroxide, or potassium hydroxide, or other alkali solutions.

Additionally, the method can also have a pretreatment step that decreases the maternal DNA that is released into the seed solution. The pretreatment can be at least one soaking of the intact seed, prior to the exposure of the seed's endosperm to encourage the release of the maternal DNA from the outer portion of the seed.

In one embodiment, the pretreatment can be a pretreatment of the seed to inhibit the release of the maternal DNA. The pretreatment can be with an alkali solution or it can be a seed coating or spray on the outer portion of the seed. In one embodiment, the pretreatment can be spraying with metallic paint.

The method can also include the step of using a prior art device to expose the seed endosperm. In one embodiment, the tip of the seed is removed. In one embodiment, the device used is a laser. In one embodiment, the device used is a knife. In one embodiment, the device used is a razor blade. In one embodiment, the device used is an automated seed cutting system.

The exposure can therefore be formed by the removal of a small portion of the seed, or by a tunnel through the seed's endosperm, or by cutting a wedge portion out of the seed leaving a portion of the endosperm exposed. In one embodiment, floury endosperm is exposed.

There is provided a method for analyzing a population of seeds: the step of pretreating at least once, an intact seed of the population forming an intact seed solution, thereby reducing the presence of maternal DNA from the outer portion of the exposed seed in the seed soak solution. Hence, in one embodiment, the amount of DNA released into the soaking solution can be reduced by a "two step" soaking approach. In one embodiment, the amount of pericarp (maternal) DNA from the outer portion of the seed released into the second soaking solution is significantly lower. In one embodiment, only the allele present in the endosperm tissue is detectable in the second soak solution.

The method for analyzing a population of seeds wherein the non-disruptive solution is a non-disruptive DNA releasing or isolating solution. Such a non-disruptive DNA releasing or isolating solution is an alkali solution. The method can employ a sodium hydroxide solution. Alternative solutions include other alkali solutions such as potassium hydroxide, and the like. The seeds remain viable at all times.

In one embodiment, the seeds are removed and dried after soaking in solution. In one embodiment, the seeds can then be stored for at least one week. In one embodiment, DNA which is released into the soaking solution can be concentrated using isopropanol.

In some embodiments the seed soak solution is used for determining the genotypic character or the phenotypic character of the seeds in the population with the seed solution isolated from the exposed viable seed.

The method includes diagnosing if one or more seeds from the population exhibits the presence or absence of the one or more traits of interest; and (optionally) sorting seeds. The isolated DNA in the seed soak solution can be tested for one or more traits of interest comprising a genetic marker, a single nucleotide polymorphism, a simple sequence repeat, a haplotype and the like.

In yet another embodiment the method for analyzing a population of seeds has one or more undesirable traits of interest as the traits of interest. In this embodiment the method has a step of sorting one or more seeds from the population of seeds based on the presence or absence of the one or more undesirable traits of interest, and discarding or retaining the sorted seeds.

Another embodiment is a bulked population of viable seeds, wherein substantially all of the seeds in the population have a portion of exposed seed endosperm wherein substantially all of the seeds in the population have the presence or absence of at least one targeted trait in common, and wherein the presence or absence of the at least one targeted trait in the seeds in the population is determined by analyzing the seed solution from the viable seed. Additionally this seed solution is not formed from a separate seed sample taken from the viable seed, but instead the seed solution is from the seed itself.

BRIEF DESCRIPTION OF THE DRAWINGS

The patent or application file contains at least one drawing executed in color. Copies of the patent or patent application publication with color drawing(s) will be provided by the Office upon request and payment of the necessary fee.

DETAILED DESCRIPTION OF THE INVENTION

Figure 1:
FIG. 1: Depiction of a corn seed with the seed tip removed from seed like the 12 seeds in Example 1. The seed has been and soaked in NaOH. The tip (not pictured) has been discarded.

Seed breeding has been made more efficient by procedures that allow the plant breeder to more clearly understand the genetic material and the allelic variants that are present or absent from breeding material. Genetic understanding of plants is gathered through analysis of either the plant's DNA or the DNA of the seed from the plant. The seed isolated DNA can be used to screen seeds for the presence or absence of the desired characteristics for the breeding populations. The present invention is a method of isolating DNA from seeds, by soaking seeds in an alkali solution to solubilize DNA, primarily from an exposed inner seed portion of the floury endosperm into the seed soaking solution forming a seed solution and a viable soaked seed with some endosperm exposed. The seed solution is mainly comprised of seed DNA from the endosperm of the soaked seed. The soaked seed are dried and the seed remains viable.

The seed solution will contain DNA. The DNA is obtained from the endosperm of the seed by soaking exposed seeds in an alkali solution, such as NaOH. Other alkali solutions can also be used in this process. The simple test for use of other solutions is to determine if the seed is soaked in the solution is the DNA quality and quantity useful for the desired testing and is the viability of the seed retained. If the solution provides these two parameters then the solution can be used. In the present embodiment of the invention the NaOH concentration is kept low and the soaking time is kept short, then the viability of soaked seeds is maintained.

The exposed seed is soaked and the seed solution will contain endosperm DNA and maternal DNA from the pericarp. Many of the tests that use the seed solution do not require the presence of maternal DNA. The amount of pericarp DNA (maternal tissue) can be reduced by pre-soaking intact seeds in alkali before exposing parts of the endosperm tissue.

Seed Priming

Seed priming is a technique of controlled hydration (soaking in water or other solution) and drying that results in more rapid germination when the seeds are reimbibed.

Seeds are soaked in a solution which disrupts cells and solubilizes DNA into the solution. Seeds are removed from the soaking solution, dried and stored. Solubilized DNA can be used to screen stored seeds for the presence of allelic variants. Based on the screening results, stored seeds can be selected and planted.

Procedure

Soaking seeds in a mild NaOH solution (2 steps):

Step 1: Soaking seeds in NaOH to disrupt pericarp cells to release maternal DNA. (Soaking solution to be discarded).

Top of the seeds is removed (e.g. razor blade, knife, laser etc.) to expose the floury endosperm.

Step 2: Soaking seeds in NaOH to solubilize DNA (mainly) from the floury endosperm into the soaking solution.

After the soaking (with or without agitation, vortexing etc.) seeds are removed from the soaking solution, dried and stored. DNA from the soaking solution can be cleaned and/or concentrated to serve as templates for e.g. molecular markers.

No seed chips have to be collected. The complexity of the two seed system is eliminated. The one seed system can be easily automated.

The seed soak solution of the present disclosure is used for testing seed for a genetic or chemical trait while preserving the germination viability of the soaked seed. The results of the testing may be diagnostic for the trait, and allows the seeds to be sorted, screened, discarded or selected. The viable seed can be planted and new seeds can be harvested from the plant and the seed soaking protocol can be performed on the new seed.

One embodiment of the seed is a maize seed, inbred, hybrid, haploid, doubled haploid, transformed, mutated etc. Any seed can be employed in the protocol if it remains viable after the exposure of the endosperm to the soaking protocol. The seed which can be used are grain seeds like maize, wheat, rice and the like, oilseeds, or vegetable, fruit or flowers seed that can maintain viability after soaking, and provide DNA quality and quantity needed for the testing.

In addition, DNA in the seed soak solution may be amplified using suitable amplification method amplification is known and products are commercially available for DNA amplification. The DNA is screened for genetic marker which may be associated with selection of QTL, haplotypes, alleles, or genes. Genetic markers include but are not limited to single nucleotide polymorphisms, simple sequence repeats and the like. Testing can employ DNA and RNA sequence material, promoters, genes, untranslated regions of genes, satellites, chips with markers, transcription profiles, methylation patterns, alleles and the like.

The testing is often looking for agronomic traits like yield, emergence, lodging, height, maturity, disease resistance, pest resistance. This testing can also identify resistance or susceptibility to biotic and abiotic stresses, resistance to herbicides, and morphological characteristics. The testing can diagnose the presence or absence of other traits for food or industry uses. The testing can be used to detect the zygosity of the embryo, or the presence of a transgene. The testing can be used for trait introgression, or purity or ploidy testing.

Selection of a breeding populations can be initiated based on the testing results. After the seed solution is formed from the soaked seed, the soaked seed is dried. The dried soaked seeds can be bulked with all desired seed of the population planted in a breeding nursery or separated with the specific seeds being identified when planted. Seed selection and the number of cycles of breeding depends on the trait and the breeding methods employed. If the seed being selected is an inbred then the steps of the breeding process may include crossing the selected seed with another inbred to form hybrid seed. Depending on the desired test the soaking protocol can be used on seeds with germplasm including hybrid seed as well. Maize seed is particularly useful for this soaking protocol.

The identification of the tested viable seed allows for a reduced use of time, energy and effort by the breeder. Additionally, it results in less land use or more populations on the same land.

The following examples serve to illustrate the invention but should not be regarded as limiting the scope of the invention.

EXAMPLES

Example 1

Comparison of Allelic Profiles from Seed and Leaf DNA

A total of 12 corn seeds had their tips removed with a razor blade to expose floury endosperm. The seeds were placed into 500 ul of 20 mM NaOH for 2 hours, with constant vortexing (FIG. 1).

After two hours, seeds were removed and dried at 30 C in an incubator, then stored at room temperature for one week.

DNA which was released into soaking solution was concentrated via isopropanol precipitation.

Figure 2:
FIG. 2: Depiction of plants which have germinated from the seeds of Example 1.

Seeds were planted into single pots in the greenhouse. All seeds germinated and produced plants (FIG. 2). At the 3 leaves stage, leaf tissue was harvested for DNA isolation. DNA from soaking solution and from leaf tissue was used to run molecular markers (Taqman assays). Allelic calls from seed DNA and leaf DNA were compared.

Figure 3:
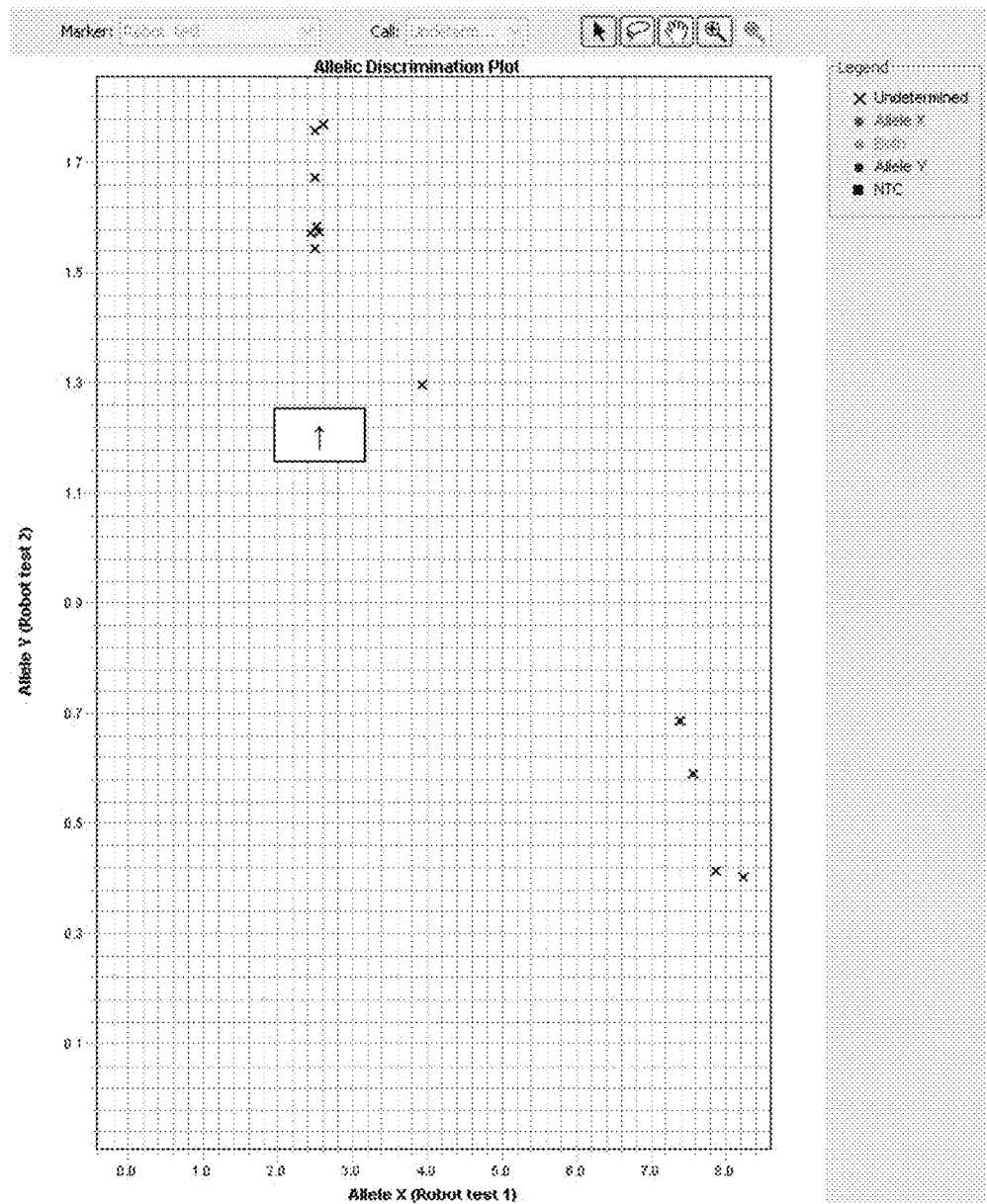
FIG. 3: Allelic discrimination plot assay 1 of Example 1, DNA obtained from seeds. The arrow is marking the mismatched sample. The 'X's in the upper left are alleles Y (not undetermined) and 'X's in the lower right are alleles X (not undetermined). The Y-axis reads "Allele Y (Robot test 2)" and the X-axis reads "Allele X (Robot test 1)" in the graph of FIG. 3, and in all the other figures with allelic discrimination plots.
Figure 4:
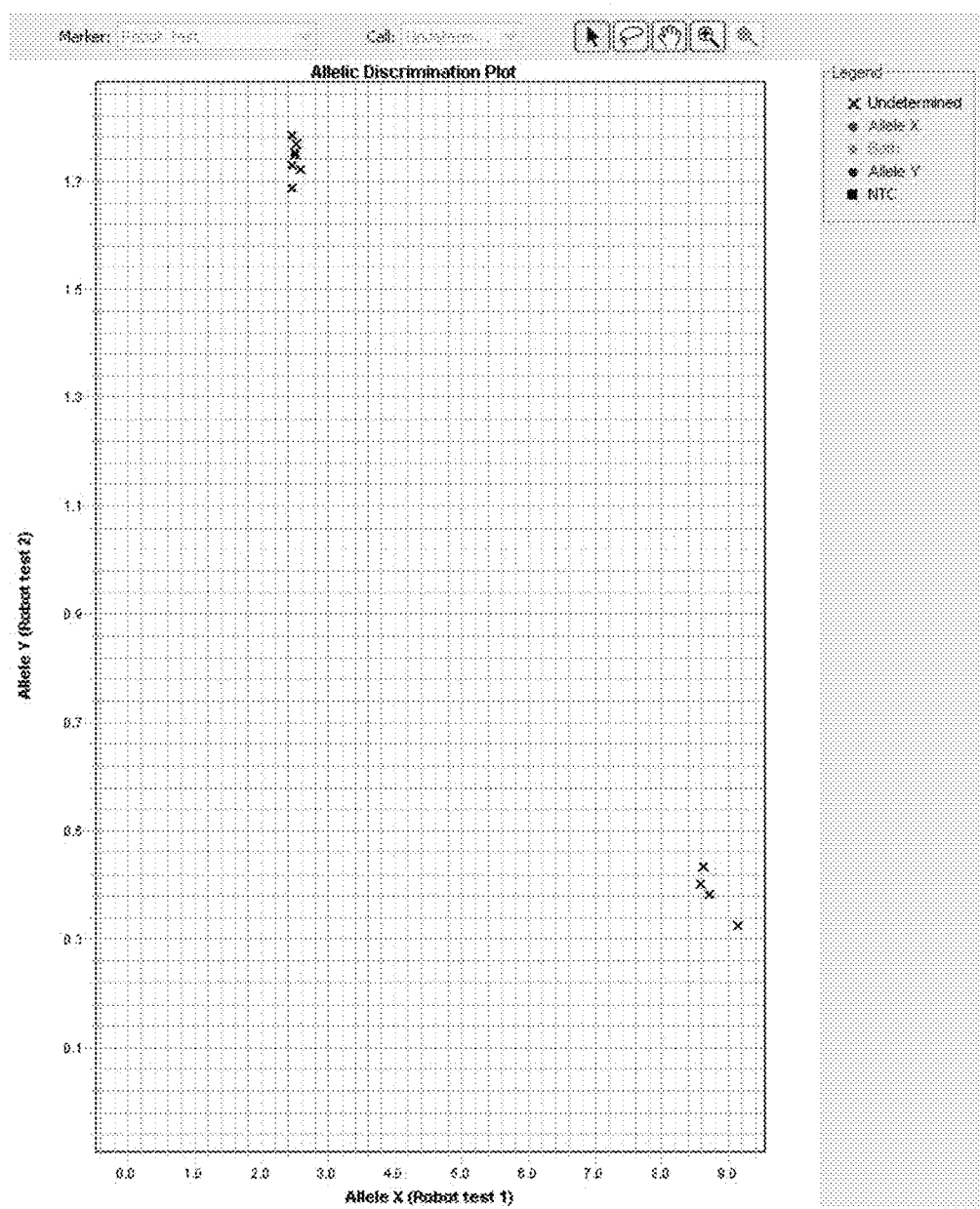
FIG. 4: Allelic discrimination plot assay 1, DNA extracted from leave tissue. The 'X's in the upper left are alleles Y (not undetermined) and 'X's in the lower right are alleles X (not undetermined).

Results:
Assay 1: Allele calls from seed and leaf DNA matched for all 12 plants (FIG. 4).
Assay 2: Allele calls from seed and leaf DNA matched for 11 plants (FIG. 3),
One mismatch was observed in which the locus was called heterozygous for seed DNA, homozygous for leaf DNA
Explanation: Allelic difference between endosperm tissue and pericarp tissue (maternal tissue) DNA.
Conclusions: DNA can be obtained from an alkali solution in which seeds were soaked; seeds can be dried and stored; seeds are viable; and pericarp DNA might cause mismatches between allelic calls from seeds and plants.

Example 2

Release of Pericarp DNA into Soaking Solution

Figure 5:
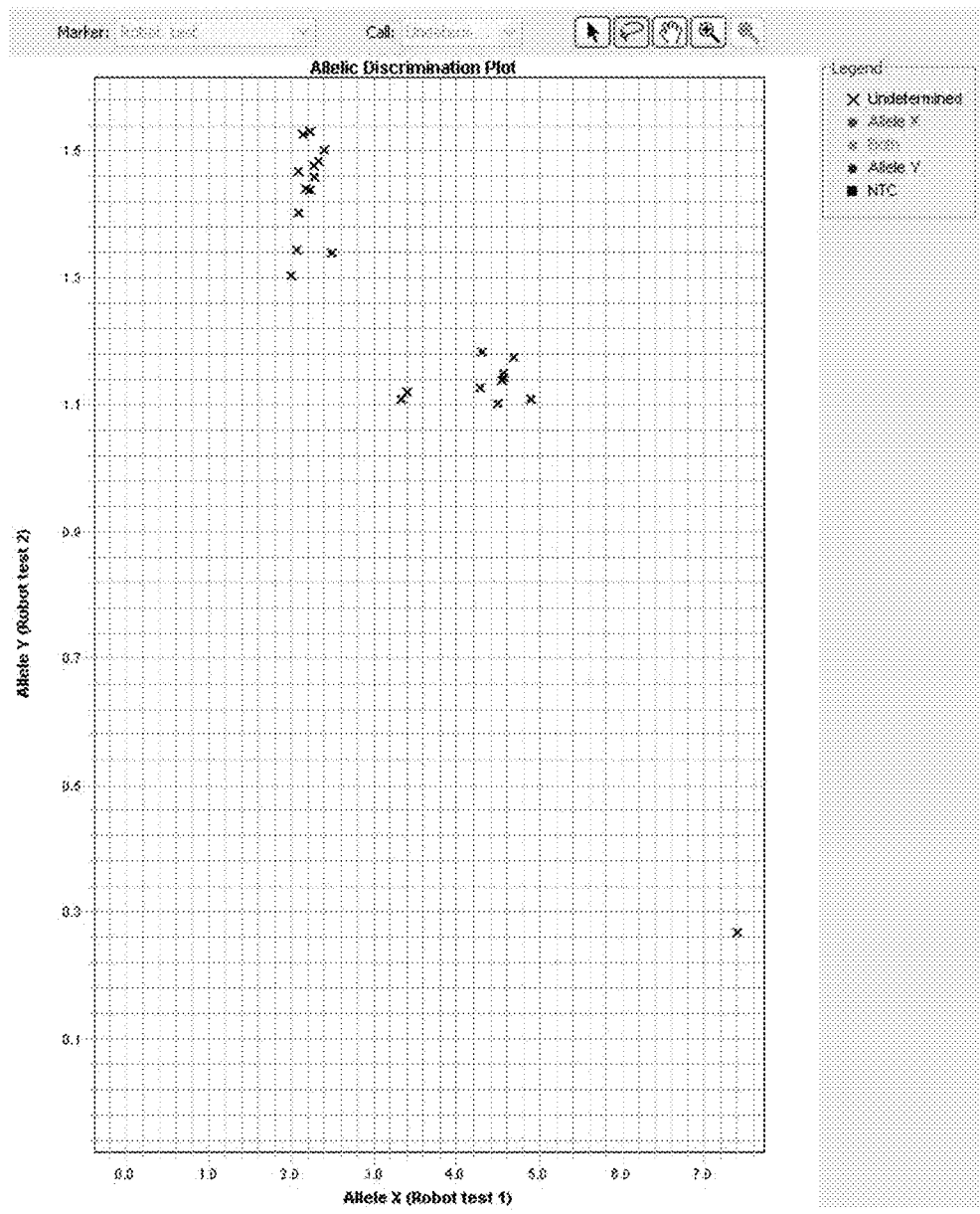
FIG. 5: Allelic discrimination plot, DNA obtained from soaking solution. Each sample tested with two DNA concentrations.

The purpose of the next experiment was to show that a significant amount of DNA is released from pericarp tissue into the NaOH soaking solution.
12 Corn seeds (tip not removed, i.e. endosperm tissue not exposed) were placed in 500 ul 20 mM NaOH.
The tubes were agitated for 2 hours at room temperature;
After two hours, seeds were removed from the soaking solution and released DNA was concentrated via isopropanol concentration; and
DNA obtained from soaking solution was used to run assay 1
The results are shown in FIG. 5, which shows an allelic discrimination plot of DNA obtained from soaking solution. Each sample was tested with two DNA concentrations.
The conclusion from this experiment was that a significant amount of DNA from pericarp tissue is released into the soaking solution.

Example 3

Reduction in Amount of Isolated Pericarp DNA

Figure 6:
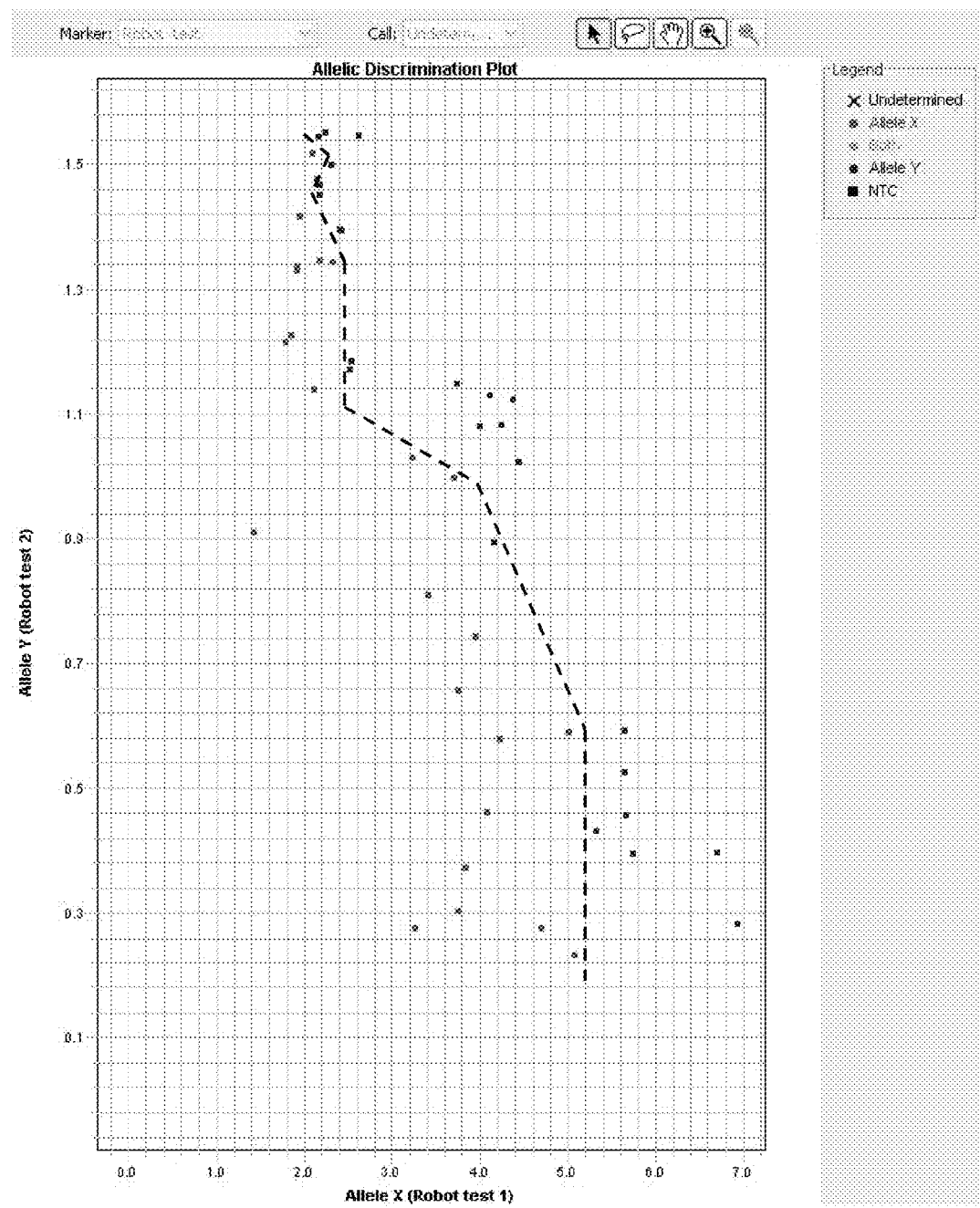
FIG. 6: Allelic discrimination plot assay 1, (blue dots: DNA obtained from first soaking solution, red dots: DNA obtained from second soaking solution, each sample tested with two DNA concentrations. Points on the plot to the left of the added dotted line correspond to blue dots. Points on the plot to the right of the added dotted line correspond to red dots.

The purpose of the next experiment was to test a method which should reduce the amount of isolated pericarp DNA.
12 corn seeds (tips not removed, i.e. endosperm tissue not exposed) were placed in 500 ul of 20 mM NaOH;
The tubes were agitated for 1 hour at room temperature;
After 1 hour seeds were removed into a second tube containing 500 ul of 20 mM NaOH and agitated for 1 hour;
After 1 hour, the seeds were removed from the second tube;
Released DNA from the first and second soaking was concentrated via isopropanol precipitation.
Results
FIG. 6 shows the results of the experiment of Example 3. It shows the allelic discrimination plot assay 1, (blue dots: DNA obtained from first soaking solution, red dots: DNA obtained from second soaking solution) Each sample tested with two DNA concentrations.

Example 4

Further Reduction in Pericarp DNA

Figure 7:
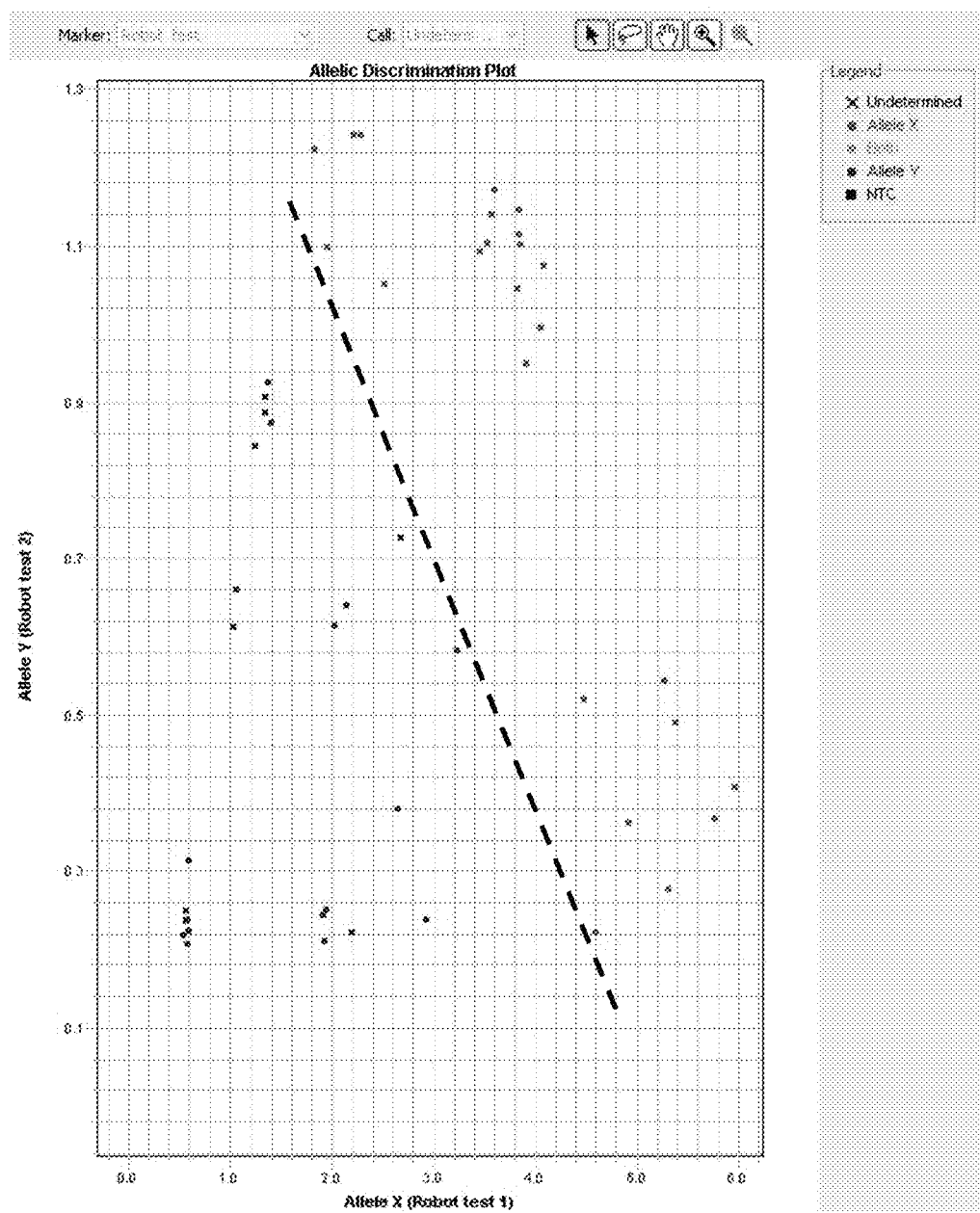
FIG. 7: Allelic discrimination plot assay 1. Blue dots: DNA obtained from first soaking solution, red dots: DNA obtained from second soaking solution. Each sample tested with two DNA concentrations. Points on the plot to the left of the added dotted line correspond to blue dots. Points on the plot to the right of the added dotted line correspond to red dots.

The purpose of the next experiment was the same as for experiment 3 but with modifying the soaking procedure to reduce isolated pericarp DNA further.
12 Corn seeds (tips not removed, i.e. endosperm tissue not exposed) were placed in 500 ul of 20 mM NaOH;
Tubes were agitated for 1.5 hours at room temperature;
After 1.5 hours seeds were removed into a second tube containing 500 ul of 10 mM NaOH and agitated for 0.5 hours;
After 1 hour seeds were removed from the second tube;
Released DNA from the first and second soaking was concentrated via isopropanol precipitation.
The results of experiment 4 are shown in FIG. 7, which shows an allelic discrimination plot assay 1. Blue dots indicate DNA obtained from first soaking solution. The red dots indicate DNA obtained from second soaking solution. Each sample tested with two DNA concentrations.
The conclusion of experiments 3 & 4 are that the amount of DNA released into the soaking solution can be reduced by a "two-step" soaking approach Example 5

Increased Efficiency of Two-Step Soaking Process

Figure 8:
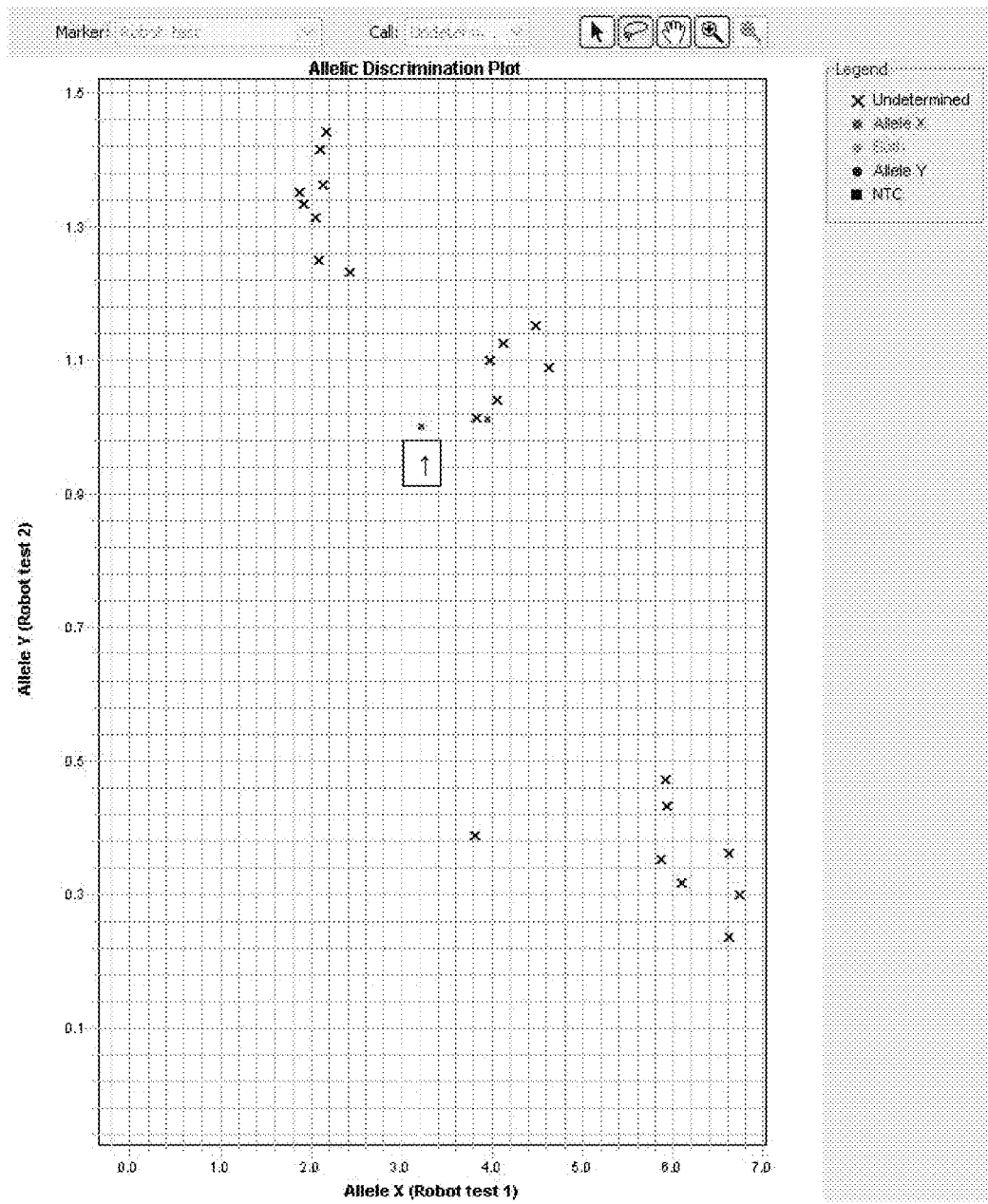
FIG. 8: Allelic discrimination plot, assay 1. DNA template: DNA obtained from the first soaking solution. Each sample tested with 2 DNA concentrations. The sample with circles and marked with the arrows are allelic mismatch between first and second soaking solution.
Figure 9:
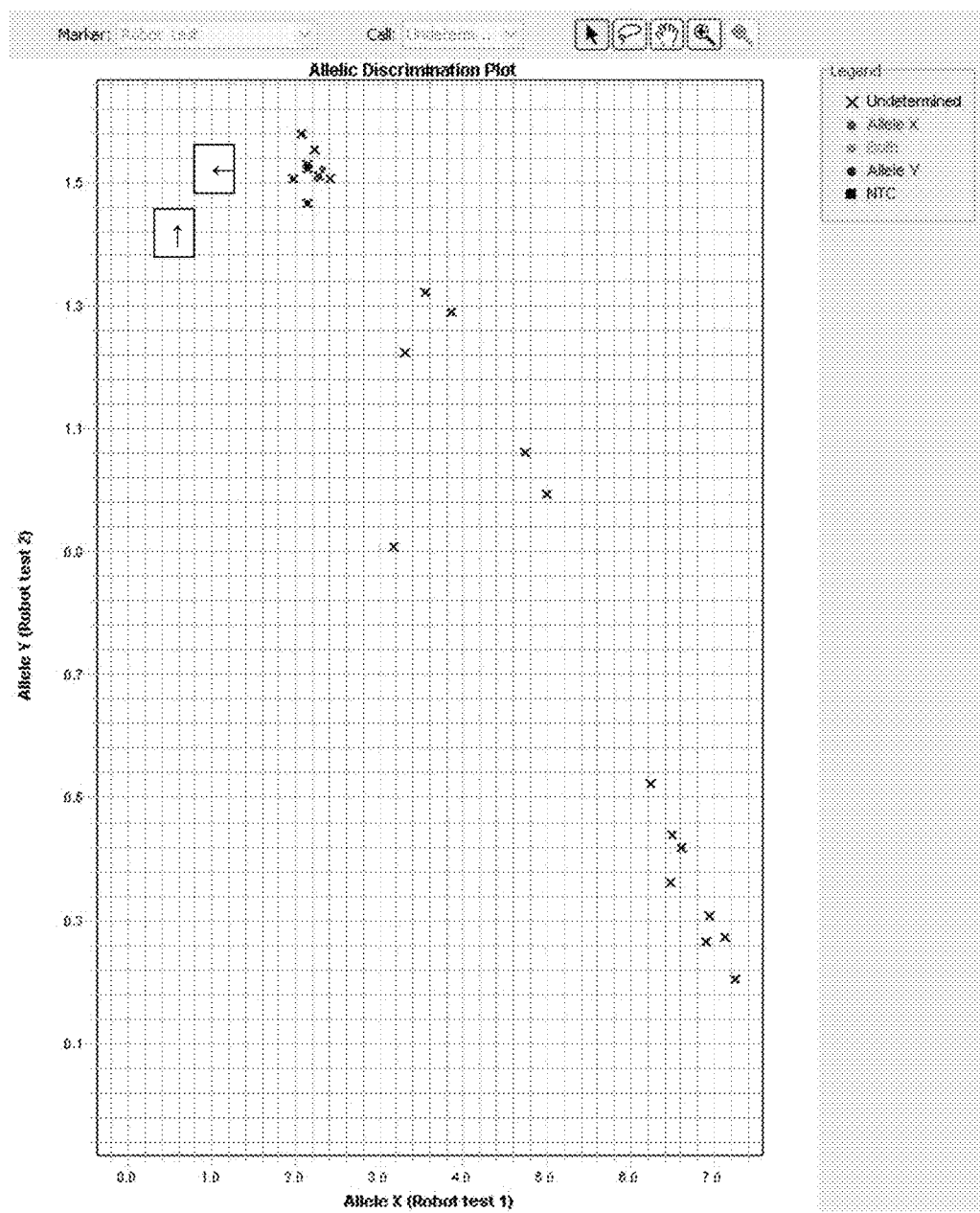
FIG. 9: Allelic discrimination plot, assay 1. DNA template: DNA obtained from the second soaking solution. Each sample tested with 2 DNA concentrations. The sample with circle dots and marked with arrows are allelic mismatch between first and second soaking solution.

The purpose of the next experiment was to measure the effect of the 2 step soaking approach on DNA isolation from seeds on predictive accuracy.
12 Seeds (floury endosperm not exposed) were soaked in 20 mM NaOH for 1.5 hours (vortexing) at room temperature;
Seeds were removed from the soaking solution, briefly dried and the floury endosperm of each seed was exposed by removing the outer seed tissue of the seed tip with a razor blade. Seeds were then placed into a second tube containing 500 ul 10 mM NaOH and vortexed at room temperature for 0.5 hours;
Seeds were removed, briefly rinsed in 0.5 mM Tris and water, dried overnight at 30 C in an incubator and then stored at room temperature for one week;
DNA released into the first and second soaking solution was concentrated via isopropanol precipitation.
Results are shown in FIG. 8 and FIG. 9.
FIG. 8 is showing an allelic discrimination plot, assay 1. The DNA template used was DNA obtained from the first soaking solution. Each sample tested with 2 DNA concentrations. The sample with circles and marked with the arrows are allelic mismatch between first and second soaking solution. FIG. 9 is showing an allelic discrimination plot, assay 1. DNA template: DNA obtained from the second soaking solution. Each sample tested with 2 DNA concentrations. The sample with circle dots and marked with arrows are allelic mismatch between first and second soaking solution.
Conclusion from experiment 5: Additional allele from pericarp tissue which is not present in endosperm tissue is released into the soaking solution. Amount of pericarp DNA released into soaking solution 2 is significantly lower, only the allele present in the endosperm tissue is detected.

Example 6

Comparison of Allelic Calls from Seed DNA and Leaf Tissue DNA

Purpose: Comparing allelic calls from DNA obtained from seeds (2 step soaking approach) and the DNA isolated from leaf tissue of germinated seeds.

Figure 10:
FIG. 10: Depiction of seeds before planting.
Figure 11:
FIG. 11: Germinated seeds shown in FIG. 10.

12 Seeds from experiment 5 were planted into single pots in a green house. The soaked and dried seeds without the seed tops exposing the endosperm. See FIG. 10. All seeds germinated. See FIG. 11.

Figure 12:
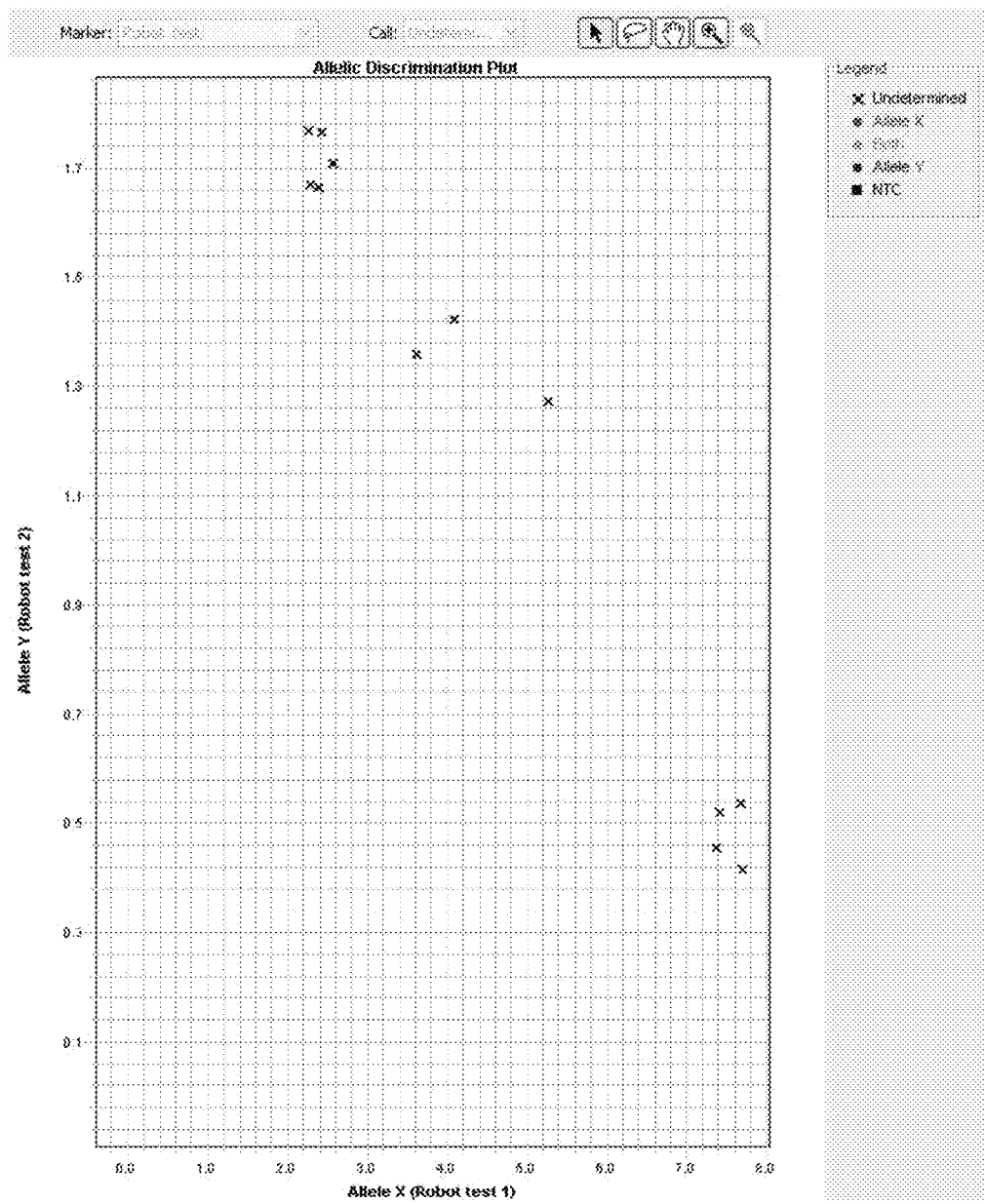
FIG. 12: Allelic discrimination plot, assay 1. DNA obtained from seeds (second soaking solution).
Figure 13:
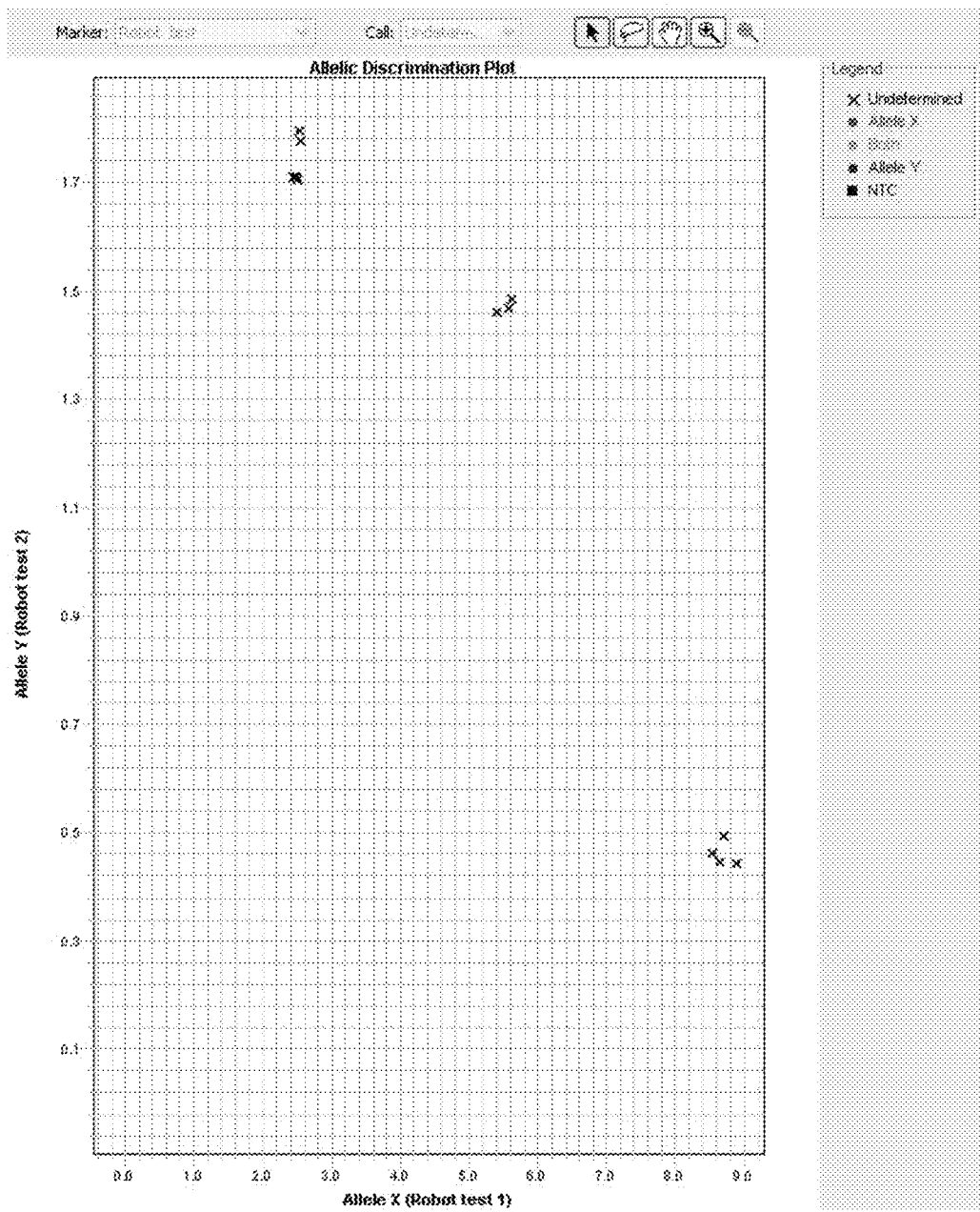
FIG. 13 shows an allelic discrimination plot, assay 1, DNA extracted from leave tissue.

Results FIG. 12 shows an allelic discrimination plot, assay 1. DNA obtained from seeds (second soaking solution). And FIG. 13 shows an allelic discrimination plot, assay 1, DNA extracted from leave tissue.

Figure 14:
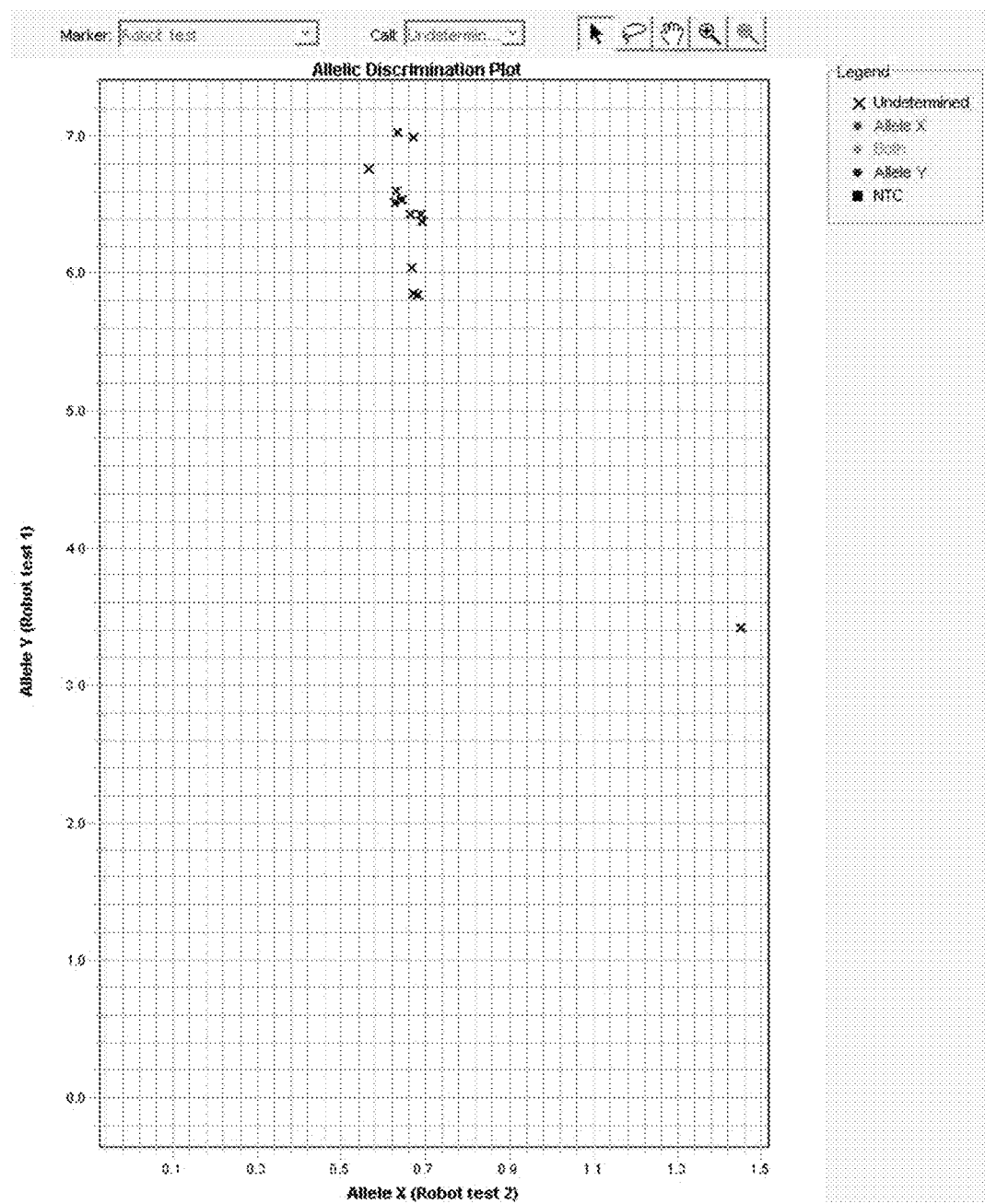
FIG. 14: Allelic discrimination plot, assay 2, DNA obtained from seeds (second soaking solution).
Figure 15:
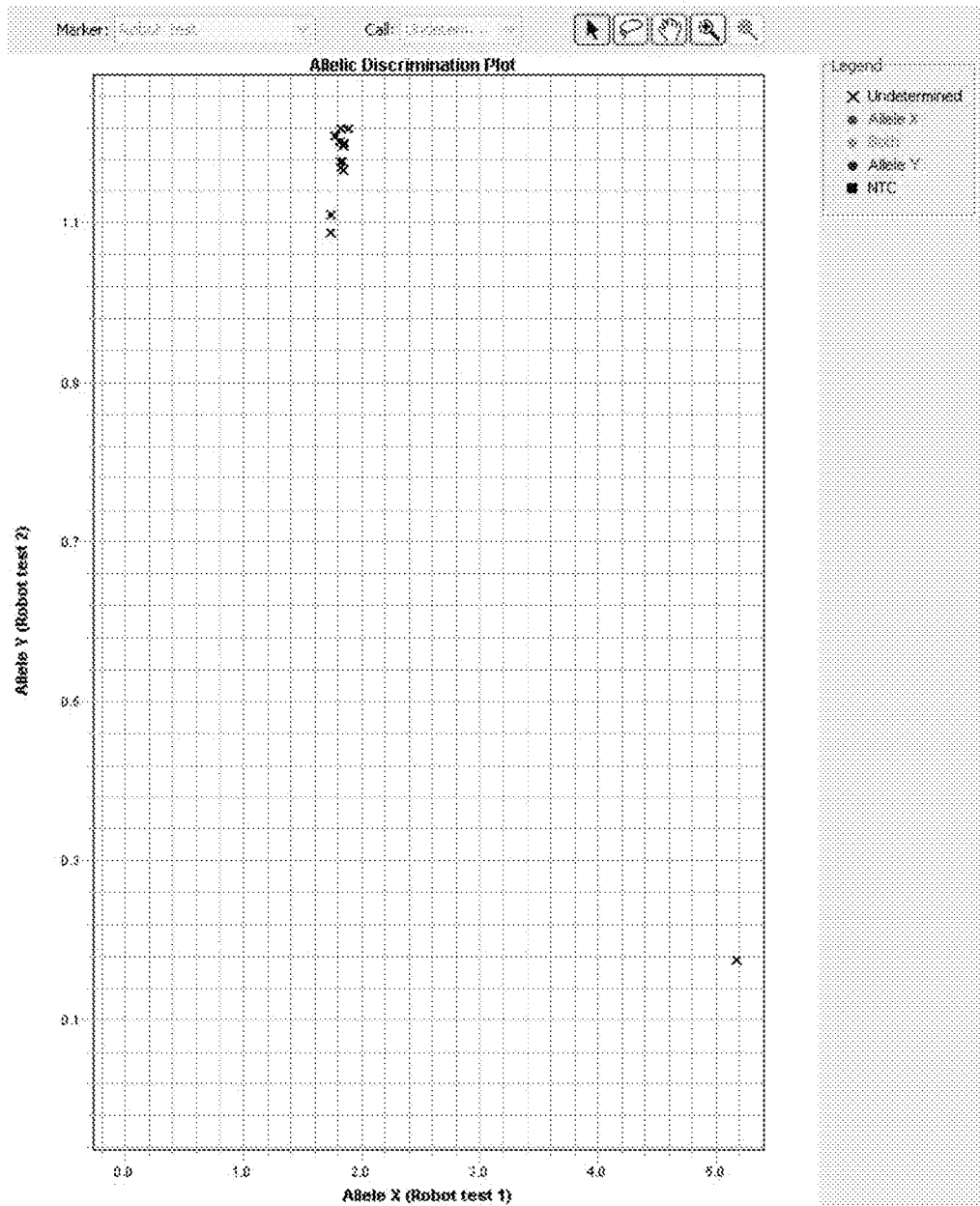
FIG. 15: Allelic discrimination plot, assay 2, DNA extracted from leave tissue.
Figure 16A:
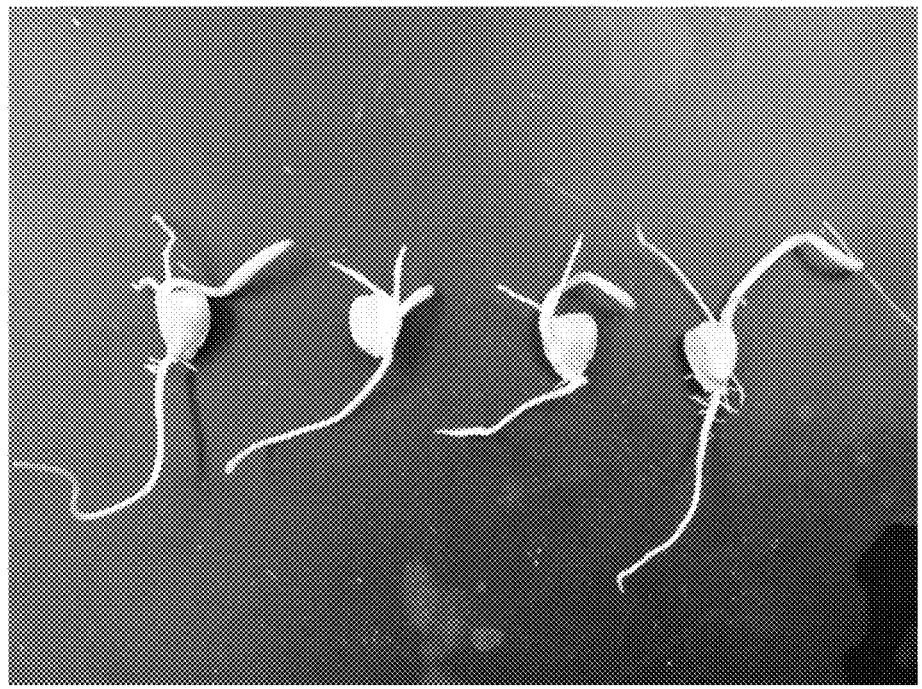
FIGS. 16A & B: Depiction of the germinated seeds which were sprayed as a pretreatment to lessen isolation of maternal DNA.
Figure 16B:
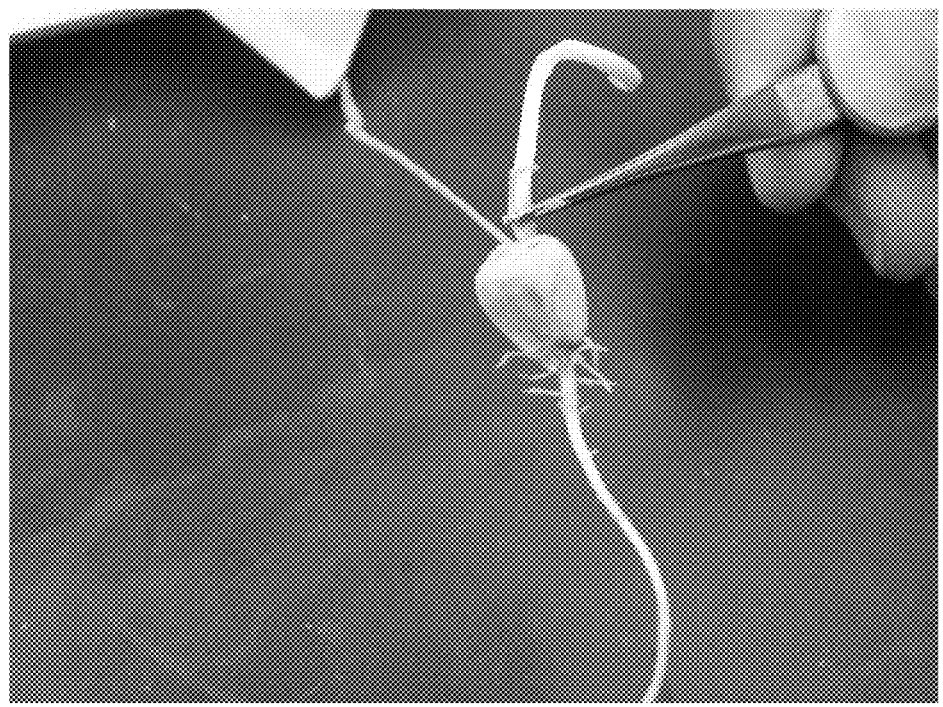

FIG. 14 shows an allelic discrimination plot, assay 2, DNA obtained from seeds (second soaking solution). And FIG. 15 shows an allelic discrimination plot, assay 2, DNA extracted from leaf tissue.

Final Results: Allelic calls match of seed DNA and leaf DNA match for both assays tested.

Conclusion from experiment 6: Allelic calls of plants can be accurately predicted by soaking seeds in alkali before planting.

Example 7

Germination Capabilities of Pretreated Seed

To prevent release of pericarp DNA into soaking solution the seed without the endosperm being exposed can be pretreated. One pretreatment is by spraying seeds with a solution before seed cutting and soaking. Below is an example: seeds were sprayed with magnetic paint before removing the top of seeds. Sprayed seeds did germinate in paper towel.

The invention claimed is:

1. A method for analyzing a population of seeds, the method comprising:
   (a) exposing the seed endosperm from individual seeds in a population of seeds while preserving germination viability of the seeds, thereby obtaining at least one viable seed with exposed endosperm;
   (b) soaking the at least one viable seed with exposed endosperm in a non-disruptive DNA-releasing alkali solution thereby forming a seed soak solution comprising DNA; and
   (c) analyzing the seed soak solution for the presence or absence of DNA indicative of the presence or absence of one or more traits of interest.

2. The method for analyzing a population of seeds according to claim 1, comprising prior to step (a): the step of pretreating, at least once, individual seeds in the population of seeds to reduce the presence of maternal DNA from the outer portion of the individual seeds.

3. The method for analyzing a population of seeds according to claim 1, comprising analyzing the DNA in the seed soak solution to determine the genotype of the viable seed with the exposed endosperm.

4. The method for analyzing a population of seeds according to claim 1 further comprising: diagnosing if one or more seeds from the population exhibits the presence or absence of the one or more traits of interest; and sorting the seeds.

5. The method for analyzing a population of seeds according to claim 1, wherein the isolated DNA in the seed soak solution is tested for one or more traits of interest comprising a genetic marker, a single nucleotide polymorphism, a simple sequence repeat, or a haplotype.

6. The method for analyzing a population of seeds according to claim 1, wherein the one or more traits of interest include one or more undesirable traits of interest; the method further comprising sorting one or more seeds from the population of seeds based on the presence or absence of the one or more undesirable traits of interest, and discarding the sorted seeds.

* * * * *